(12) United States Patent
Lee et al.

(10) Patent No.: US 7,638,642 B2
(45) Date of Patent: *Dec. 29, 2009

(54) METHOD FOR THE PREPARATION OF D-ERYTHRO-2,2-DIFLUORO-2-DEOXY-1-OXORIBOSE DERIVATIVE

(75) Inventors: Jaeheon Lee, Yongin-si (KR); Gha-Seung Park, Yongin-si (KR); Moonsub Lee, Daejeon (KR); Cheol-Kyong Kim, Suwon-si (KR); Jae-Chul Lee, Suwon-si (KR); Young-Kil Chang, Seoul (KR); Gwan-Sun Lee, Seoul (KR)

(73) Assignee: Hanmi Pharm, Co., Ltd, Hwaseong-gun (KR)

( * ) Notice: Subject to any disclaimer, the term of this patent is extended or adjusted under 35 U.S.C. 154(b) by 204 days.

This patent is subject to a terminal disclaimer.

(21) Appl. No.: 11/572,404

(22) PCT Filed: Jun. 23, 2005

(86) PCT No.: PCT/KR2005/001955

§ 371 (c)(1),
(2), (4) Date: Jan. 19, 2007

(87) PCT Pub. No.: WO2006/009353

PCT Pub. Date: Jan. 26, 2006

(65) Prior Publication Data

US 2008/0058509 A1  Mar. 6, 2008

(30) Foreign Application Priority Data

Jul. 23, 2004  (KR) .................... 10-2004-0057711

(51) Int. Cl.
*C07D 307/02* (2006.01)
(52) U.S. Cl. ...................................................... 549/477
(58) Field of Classification Search ................ None
See application file for complete search history.

(56) References Cited

U.S. PATENT DOCUMENTS

| 4,526,988 | A | 7/1985 | Hertel |
| 4,965,374 | A | 10/1990 | Chou et al. |
| 5,223,608 | A | 6/1993 | Chou et al. |
| 5,401,861 | A | 3/1995 | Chou et al. |
| 5,428,176 | A | 6/1995 | Weigel |
| 5,434,254 | A | 7/1995 | Chou et al. |
| 5,453,499 | A | 9/1995 | Chou et al. |
| 5,618,951 | A | 4/1997 | Britton |
| 5,945,547 | A | 8/1999 | Chou et al. |

OTHER PUBLICATIONS

Corey et al. Journal of the American Chemical Society 93:6, Mar. 24, 1971, pp. 1491-1493.*
Greene et al. Protective Groups in Organic Synthesis, Third Edition. John Wily & Sons, 1999, pp. 150-160.*

* cited by examiner

*Primary Examiner*—Shaojia Anna Jiang
*Assistant Examiner*—Layla Bland
(74) *Attorney, Agent, or Firm*—Sughrue Mion, PLLC

(57) ABSTRACT

3R-carboxylate enantiomer derivative of formula (III) can be prepared easily and selectively by the method of the present invention, and a highly pure D-erythro-2,2-difluoro-2-deoxy-1-oxoribose derivative can be prepared efficiently from the compound of formula (III) as an intermediate.

8 Claims, No Drawings

METHOD FOR THE PREPARATION OF D-ERYTHRO-2,2-DIFLUORO-2-DEOXY-1-OXORIBOSE DERIVATIVE

FIELD OF THE INVENTION

The present invention relates to a method for preparing highly pure D-erythro-2,2-difluoro-2-deoxy-1-oxoribose derivatives.

BACKGROUND OF THE INVENTION

D-erythro-2,2-difluoro-2-deoxy-1-oxoribose is an important intermediate used in the preparation of gemcitabine of formula (A), an agent for treating non-small cell lung cancer.

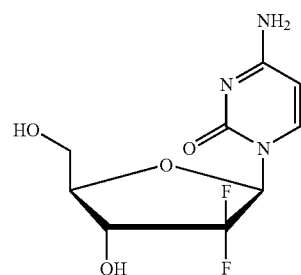

(A)

Since gemcitabine is an erytliro enantiomer having the 3-hydroxy moiety oriented down (opposite to the 5-hydroxy group with respect to the place of the tetrahydrofuran ring), it is important in the preparation of gemcitabine to develop a method for preparing 1-oxoribose erythro compounds having the 3-hydroxy group oriented down.

U.S. Pat. No. 4,526,988 discloses a method for preparing an erythro 1-oxoribose compound via alkyl 2,2-difluoro-3-hydroxy-3-(2,2-dialkyldioxoran-4-yl)propionate, a 3:1 mixture of 3R-hydroxy enantiomer of formula (B) and 3S-hydroxy enantiomer of formula (B')

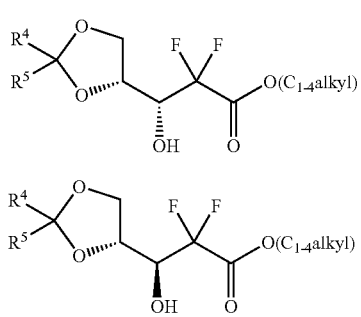

wherein,
$R^4$ and $R^5$ are each independently $C_{1-3}$ alkyl.

However, such a method involves an uneconomical step of isolating only the 3R-hydroxy enantiomer of formula (B) from the mixture of the compounds of (B) and (B') in order to selectively prepare the desired erythro 1-oxoribose derivative, because the compounds of (B) and (B') produce an erythro compound of formula (C) and a threo compound of formula (C'), respectively, as shown in Reaction Scheme A and B.

Reaction Scheme A

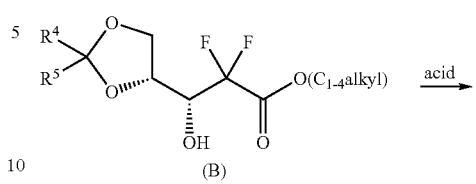

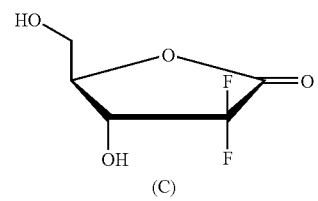

Reaction Scheme B

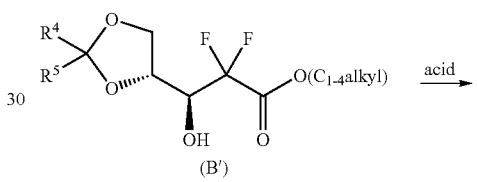

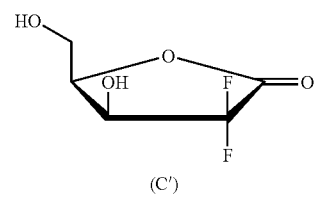

Further, the method also has the problem that it takes a long reaction time, almost four days at room temperature.

Meanwhile, U.S. Pat. Nos. 4,965,374; 5,223,608; and 5,434,254 disclose a method for obtaining an erythro enantiomer of formula (D), as shown in Reaction Scheme C, by (i) hydrolyzing and azeotropically distilling a 3-benzoyloxypropionate ester of formula (E) (a 3:1 mixture of 3R- and 3S-enantiomers) to obtain a lactone compound of formula (F); (ii) protecting the 5-hydroxy group of the compound of formula (F) with benzoyl to obtain a 3,5-dibenzoyloxy compound of formula (G); and (iii) cooling the compound of formula (G) to −5~10° C. to precipitate only the erythro enantiomer of formula (D).

Reaction Scheme C

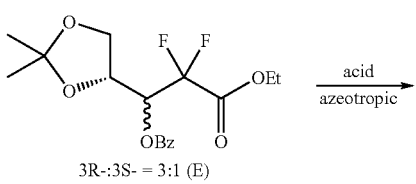

3R-:3S- = 3:1 (E)

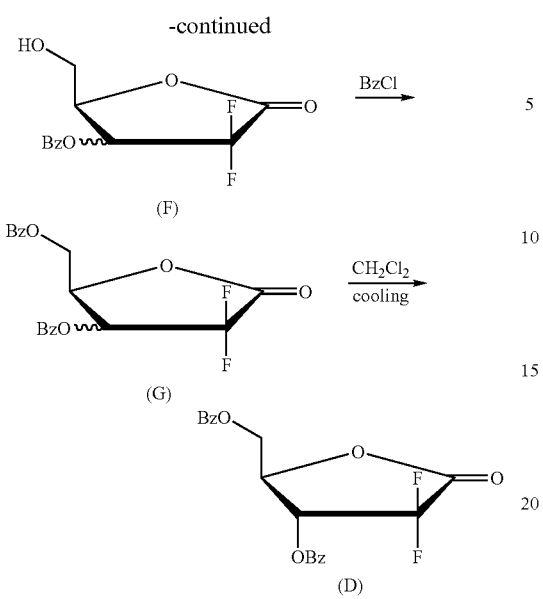

wherein, Bz is benzoyl.

However, the above method is uneconomical due to its overall low yield of about 25% and the use of an expensive and toxic trifluoroacetic acid in an excess amount in the hydrolyzing process.

Further, U.S. Pat. Nos. 5,428,176 and 5,618,951 teach a method of preparing a 2,2-difluoro-β-silyloxy-1,3-dioxolane-4-propionic acid ester of formula (H) having a high 3R-silylhydroxy enantiomer content by reacting a 2,2-difluoroketene silyl acetal with a glyceraldehyde derivative in a solvent such as 1,3-dimethylpropylene urea (DMPU), as shown in Reaction Scheme D.

Reaction Scheme D

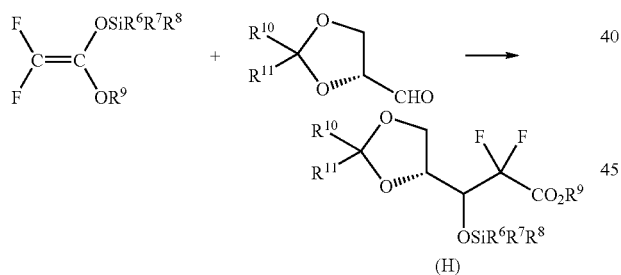

wherein, $R^6$ to $R^9$ are alkyl; and $R^{11}$ and $R^{11}$ are $C_{1-3}$ alkyl.

However, this method also requires an uneconomical column chromatography process for isolating the 3R-enantiomer from the mixture of the enantiomers.

Accordingly, the present inventors have endeavored to develop an efficient method for selectively preparing 1-oxoribose compounds having an erythro structure, and have unexpectedly found an efficient, novel method for preparing highly pure 2,2-difluoro-2-deoxy-1-oxoribose having an erytiro structure.

SUMMARY OF THE INVENTION

Accordingly, it is an object of the present invention to provide an efficient method for selectively preparing 2,2-difluoro-2-deoxy-1-oxoribose derivatives having an erythro structure.

It is another object of the present invention to provide a 3R-enantiomer compound which can be used as an intermediate in said method.

In accordance with one aspect of the present invention, there is provided a method for preparing a 2,2-difluoro-2-deoxy-1-oxoribose derivative of formula (I), comprising the steps of (i) reacting a compound of formula (V) with a biphenylcarbonyl derivative to obtain a compound of formula (IV) having the 3-hydroxy group protected by a biphenylcabonyl group; (ii) reacting the compound of formula (IV) with a base in a mixed solvent essentially comprising water to obtain a 3R-carboxylate enantiomer of formula (III); (iii) reacting the compound of formula (III) with an acid to obtain a 5-hydroxy-1-oxoribose derivative of formula (II); and (iv) protecting the 5-hydroxy group of the compound of formula (II) with $R^3$:

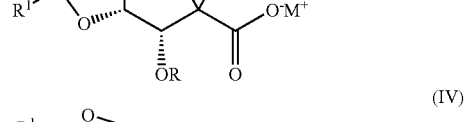

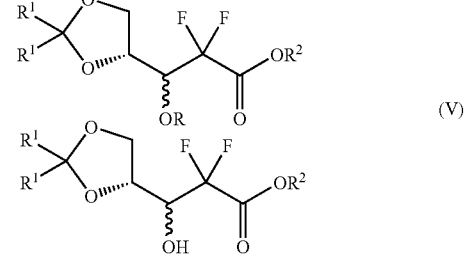

wherein, R is

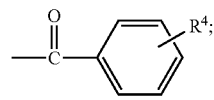

$R^1$ is methyl or ethyl;
$R^2$ is $C_{1-3}$ alkyl;
$R^3$ is benzoyl or

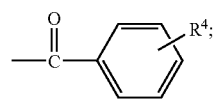

$R^4$ is phenyl or substituted phenyl; and
M is ammonium ($NH_4$), sodium or potassium.

In accordance with another aspect of the present invention, there is provided a 3R-carboxylate enantiomer of formula (III):

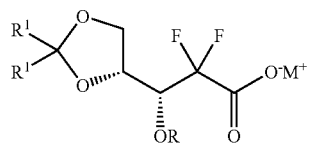

(III)

wherein, R, $R^1$, and M have the same meanings as defined above.

DETAILED DESCRIPTION OF THE INVENTION

In the inventive method, the compounds of formulas (IV) and (V) are each a mixture of 3R- and 3S- enantiomer of a given ratio.

The inventive method is summarized in Reaction Scheme I.

The inventive method is characterized in that it is possible to selectively obtain the 3R-carboxylate enantiomer of formula (III) by protecting the 3-hydroxy group of the compound of formula (V) with a biphenylcarbonyl group, and obtaining the 1-oxoribose derivative of formula (I) having a desired erythro structure therefrom.

Since the compound of formula (III) can be obtained selectively as a solid in the inventive method, it can be easily isolated using a simple filtering process without conducting an uneconomical column chromatography or other purification processes. Accordingly, the use of the compound of formula (II) as an intermediate is the unique feature of the inventive method which is suitable for a large-scale production of the 1-oxoribose derivative.

The compound of formula (V) used as a starting material in the inventive method may be prepared by a conventional method described in U.S. Pat. Nos. 4,526,988; 4,965,374; 5,223,608; and 5,434,254, as shown in Reaction Scheme II.

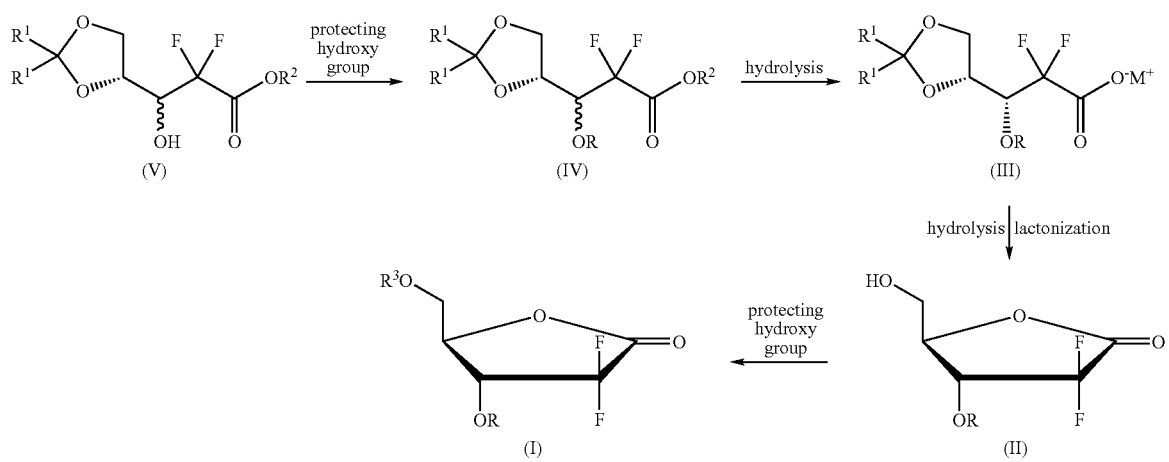

Reaction Scheme I wherein, R, $R^1$, $R^2$, $R^3$ and M have the same meanings as defined above.

In Reaction Scheme I, a 2,2-difluoro-2-deoxy-1-oxoribose derivative of formula (I) may be prepared in a high yield by protecting the 3-hydroxy group of the compound of formula (V) with biphenylcarbonyl group to obtain a compound of formula (IV); hydrolyzing the compound of formula (IV) with a base to obtain a 3R-carboxylate salt of formula (III), in which the 3R-enantiomer of formula (III) can be isolated from the resulting mixture of 3R- and 3S-enantiomers because only the 3R-enantiomer is obtained as a solid; deprotecting the dioxolane group of the compound of formula (III) with an acid to obtain a carboxylic acid derivative, and lactonizing the carboxylic acid derivative with distilling-off water to obtain a 5-hydroxy-1-oxoribose of formula (II) having an erythro structure; and protecting the 5-hydroxy of the compound of formula (II) according to a conventional method.

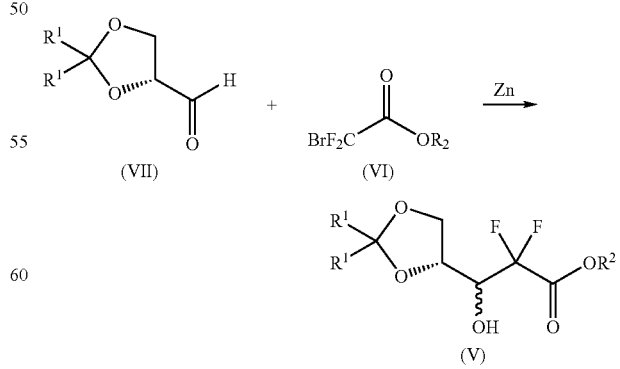

Reaction Scheme II wherein, R, $R^1$ and $R^2$ have the same meanings as defined above.

In Reaction Scheme II, the compound of formula (V), a 3:1 mixture of 3R- and 3S-enantiomers, may be prepared by mixing an aldehyde ketonide of formula (VII) with a difluoro compound of formula (VI), and allowing the mixture to undergo Reformatsky reaction using zinc.

Further, a 3R-carboxylate of formula (III) can be prepared from the compound of formula (V), as shown in Reaction Scheme III.

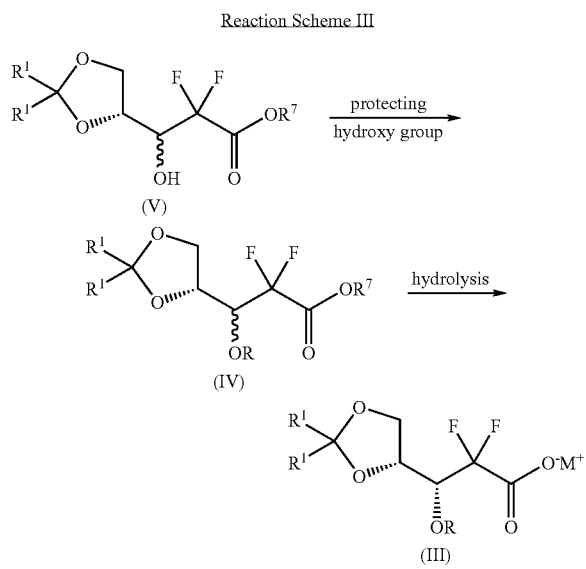

wherein, R, $R^1$, $R^2$ and M have the same meanings as defined above.

In Reaction Scheme III, the 3R-carboxylate of formula (III) can be obtained as a solid by: (i) protecting the 3-hydroxy group of the compound of formula (V) with a biphenylcarbonyl protecting group to obtain the compound of formula (IV); and (ii) hydrolyzing the compound of formula (IV) with a base.

In the inventive method, the protecting group used in step (i) may be a biphenylcarbonyl group which is a benzoyl group substituted with benzene ring optionally the benzene ring is substituted with one or more substituents selected from the group consisting of hydrogen, cyano, halo, carboalkoxy, toluoyl, nitro, alkoxy, alkyl and dialkylamino. Representative examples of biphenylcarbonyl include such as 2-phenylbenzoyl (2-biphenylcarbonyl), 4-phenylbenzoyl (4-biphenylcarbonyl) and substituted 2-(or 4-) phenylbenzoyl, preferably 2-phenylbenzoyl and 4-phenylbenzoyl.

Increased hydrophobicity due to the two benzene ring of biphenylcarbonyl group makes it possible to separate 3R-carboxylate of formula (III) as a solid even in the water or water containing mixed solvent.

On the other hand, in case of using a conventional benzoyl group as a hydroxy protecting group, it is impossible to get a 3R-carboxylate salt as a solid in the water or water containing mixed solvent.

In contrast, in case of introducing a conventional hydroxy protecting group such as 1-naphtoyl, 2-naphtoyl, pivaloyl or acetyl for the 3-hydroxy group of the compound of formula (V), it is very difficult to selectively isolate the 3R-carboxylate of formula (III) as a solid from the resulting reaction mixture.

The biphenylcarbonyl-based compound used in step (i) may be selected from the group consisting of biphenylcarbonyl (or substituted biphenylcarbonyl) chloride, bromide, cyanide or azide, which may be commercially obtained or chemically synthesized in accordance with conventional methods.

Also, the base used in the neutralization process of step (i) may be selected from the group consisting of pyridine, triethylamine, tributylamine, diisopropylethylamine and methylpiperidine, preferably triethylamine; a catalyst used in the acylation may be 4-dimethylaminopyridine or 4-pyrolidinopyridine; and the acylation may be conducted at −25 to 50° C.

In the hydrolysis of step (ii), the base may be selected from the group consisting of gaseous ammonia, aqueous ammonia, sodium carbonate, sodium bicarbonate, sodium hydroxide, potassium carbonate, potassium bicarbonate, potassium hydroxide and a mixture thereof, preferably potassium bicarbonate, which may be employed in an amount of 1 equivalent or more, preferably ranging from 1.5 to 5 equivalents based on the compound of formula (IV).

Also, the mixed solvent essentially comprising water may be a mixture of water and an organic solvent selected from the group consisting of tetrahydrofuran, dioxane, acetonitrile, acetone, methylisobutylketone, methylethylketone, methanol, ethanol, propanol, isopropanol, dimethylacetamide, dimethylformamide, dimethylsulfoxide, ethyl acetate and a mixture thereof, preferably a mixture of tetrahydrofuran and methanol; and the water may be employed in an amount ranging from 3 to 15 ml, preferably from 5 to 11 ml, and the organic solvent, from 3 to 30 ml, preferably from 6 to 18 ml, based on 1.0 g of the compound of formula (IV). The hydrolysis may be conducted at 5 to 50° C., preferably 10 to 30° C. for 30 min to 2 hours.

The compound of formula (III) may be isolated easily from the reaction mixture obtained in step (ii), by removing the organic solvent under a reduced pressure, and filtering the resulting mixture; or by extracting the reaction mixture with an organic solvent, and recrystallizing the product in a mixed solvent essentially comprising water.

In the inventive method, the 3R-carboxylate of formula (III) may be obtained from the compound of formula (V) in a high yield of 60 to 70% via a potassium or sodium salt, or about 40% when an ammonium salt is used as a base in step (ii). Further, the compound of formula (III) obtained in the inventive method has a 3R-carboxylate content of more than 99.7% while the 3S-carboxylate content is less than 0.3% (consequently, e.e value over 99.4%).

The compound of formula (I) having the erythro structure may be obtained from the compound of formula (III) in a highly enantioselective manner, as shown in Reaction Scheme IV.

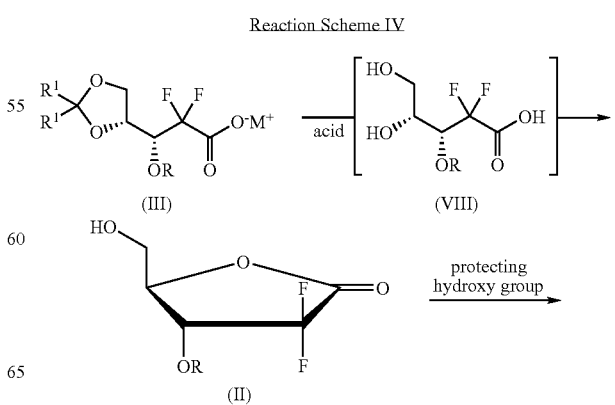

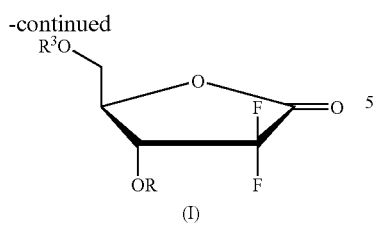

wherein, R, $R^1$, $R^3$ and M have the same meanings as defined above.

In Reaction Scheme IV, the compound of formula (I) may be prepared by (iii) reacting the compound of formula (III) with an acid in a solvent to obtain the compound of formula (II) having the erythro structure as a result of conducting the cascade of reactions comprising the neutralization of the carboxylate, removal of the isoalkylidene protecting group to produce a diol carboxylic acid of formula (VIII), and lactonization of the compound of formula (VIII); and (iv) protecting the 5-hydroxy group of the compound of formula (II) with a protecting group containing a hydrophobic benzene ring.

The acid used in the inventive step (iii) may be a strong acid having a pka value ranging from −10.0 to 2.0, which may be selected from the group consisting of an inorganic acid such as 1 to 12 N HCl and 1 to 9 N $H_2SO_4$, and an organic acid such as methanesulfonic acid, p-toluenesulfonic acid, trifluoroacetic acid and trifluoromethanesulfonic acid, preferably 12 N HCl and trifluoroacetic acid, more preferably 12 N HCl; employed in an amount ranging from 1 to 2 equivalents, preferably 1.1 to 1.5 equivalents based on the compound of formula (III).

Meanwhile, the reaction product of step (iii) may be regulated so as to comprise 1 to 10 equivalents, preferably 2 to 5 equivalents of water based on the compound of formula (III), for instance, by adding an aqueous solution thereto, e.g., an aqueous inorganic acid having an appropriate concentration, or an aqueous solvent such as 95% ethanol, in order to effectively remove the isoalkylidene group. The solvent used in step (iii) may be selected from the group consisting of acetonitrile, tetrahydrofuran, 1,4-dioxane, ethanol, methanol and isopropanol, preferably acetonitrile.

Step (iii) may be carried out at a refluxing temperature of the solvent for 4 to 8 hours to remove the isoalkylidene group; and the resulting mixture may be mixed with a solvent such as benzene and toluene, and azeotropically distilled to remove water from the reaction mixture to obtain the lactonized compound of formula (II).

In step (iv), the protecting group may be selected from the group consisting of benzoyl, phenylbenzoyl and substituted benzoyl, preferably 2-phenylbenzoyl, 4-phenylbenzoyl and substituted 2- (or 4-) phenylbenzoyl.

Also, step (iv) may be conducted after isolating the compound of formula (II) obtained in step (iii), or conducted without such an isolating process in situ. The in situ process is preferred.

The compound of formula (I) obtained in the inventive method exhibits a high purity of about 99% of the 1-oxoribose compound having the desired erythro structure.

Further, the inventive method has a total yield of 45 to 50%, which is improved more than 20% relative to the conventional methods.

The following Examples are intended to further illustrate the present invention without limiting its scope.

PREPARATION 1

Preparation of 2,2-difluoro-3-hydroxy-3-(2,2-dimethyl-[1,3]dioxoran-4-yl)propionate (compound of formula (V))

Step 1: Preparation of 1,2-bis-(2,2-dimethyl-1,3-dioxoran-4-yl)-ethane-1,2-diol

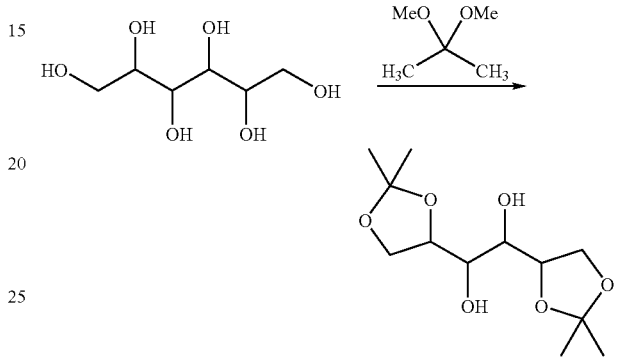

100 g of d-mannitol was mixed with 160 ml of 2,2-dimethoxypropane, 240 ml of 1,2-dimethylethanediol and 0.1 g of anhydrous $SnCl_2$, the mixture was heated until a homogeneous solution was obtained, and refluxed for 30 min, and 0.2 ml of pyridine was added thereto. The reaction mixture was cooled to room temperature, and distilled under a reduced pressure to remove the solvent. 700 ml of methylchloride was added to the residue and refluxed for 1 hour. The resulting mixture was filtered through 10 g of cellite at room temperature, and the filtrate was distilled under a reduced pressure to remove the solvent. The residue was recrystallized from 1 L of hexane, filtered, and dried to obtain 72.4 g (yield 50%) of the title compound as a white solid.

NMR (300 MHz, $CDCl_3$): 1.30(s, 6H), 1.36(s, 6H), 2.52(d, 2H), 3.67(t, 2H), 3.91(m, 2H), 4.04~4.14(m, 4H) Melting point (m.p.): 119~121° C.

Step 2: Preparation of 2,2-dimethyl-[1,3]-dioxorane-4-carboaldehyde

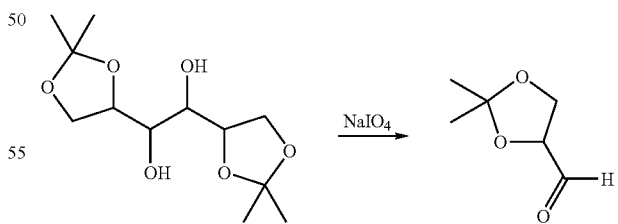

72.4 g of the compound obtained in Step 1 was dissolved in 724 ml of methylchloride, and 30 ml of saturated sodium bicarbonate was added thereto. The mixture was cooled in a water bath, and 118 g of sodium methaperiodate was added in small portion thereto over a period of 20 min while keeping the temperature at under 25° C. The reaction mixture was stirred at room temperature for 2 hours. After confirming the completion of the reaction by thin layer chromatography (TLC), 36 g of anhydrous magnesiumsulfate was added to the reaction mixture, and stirred for 20 min. The resulting mixture was filtered and distilled under a reduced pressure at 30° C. to remove the solvent, and the residue was further subjected in distillation under an atmospheric pressure at 55° C. to completely remove the solvent. The reacting residue was distilled at 10 torr, about 40° C. to obtain 61.6 g (yield 86%) of the title compound as a colorless liquid.

NMR (300 MHz, CDCl$_3$): 1.41(s, 3H), 1.47(s, 3H), 4.07~4.19(m, 2H), 4.35~4.40(m, 1H), 9.71(s, 1H)

Step 3: Preparation of ethyl 2,2-difluoro-3-hydroxy-3-(2,2-dimethyl-[1,3]dioxoran-4-yl)propionate

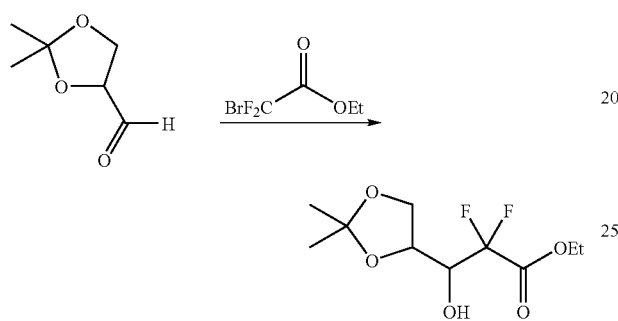

13 g of zinc was added to 26 ml of tetrahydrofuran, 0.51 ml of dibromoethane was added thereto, and the mixture was kept at 60° C. for 1 min. 0.76 ml of chlorotrimethylsilane was added thereto at 40° C., and the mixture was allowed to react for 10 min. The reaction mixture was heated to 60° C., a solution made of 25.5 ml of ethyl bromodifluoroacetate, 30.8 g of the compound obtained in step 2 and 39 ml of tetrohydrofuran was added dropwise thereto, and the mixture was refluxed for 30 min. After adding 65 ml of diethyl ether and 260 g of ice thereto, 260 ml of 1 N HCl was added thereto and stirred until the ice was completely melted. The aqueous layer was extracted three times with 90 ml portion of diethyl ether, the combined organic layer was washed successively with 65 ml portion of NaCl and sodium bicarbonate, dried over anhydrous magnesiumsulfate, and filtered. . After removing the solvent, the residue was distilled at 10 torr to obtain 28.9 g (57%) of the title compound (R:S=3:1) at 130~134° C. as a colorless liquid.

NMR (300 MHz, CDCl$_3$): 1.31~1.52(m, 9H), 2.67(s, 1H, (R)-OH), 2.90(d, 1H, (S)-OH), 3.7~4.4(m, 6H)

In the following Examples, the term "-OCOBiPh" or "BiPhOCO-" refers to

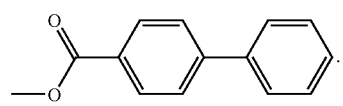

HPLC analyses of the compounds of formulas (I) and (III) were performed with a YMC pack pro C18 RS (4.6×150 mm, 5 μm) column using a mixture of a buffer and acetonitrile (65:35, v/v) (for the compound of formula (III)) or 80% acetonitrile (for the compound of formula (I)) as an eluent.

The buffer was prepared by mixing 7.0 g of NaClO$_4$, 1.74 g of K$_2$BPO$_4$ and 1 L of water, and adding H$_3$PO$_4$ thereto until pH 2.75.

EXAMPLE 1

Preparation of ethyl 2,2-difluoro-3-(4-biphenylcarbonyl)oxy-3-(2,2-dimethyl-[1,3]dioxoran-4-yl)propionate (the compound of formula (IV); R=4-bicarbonyl)

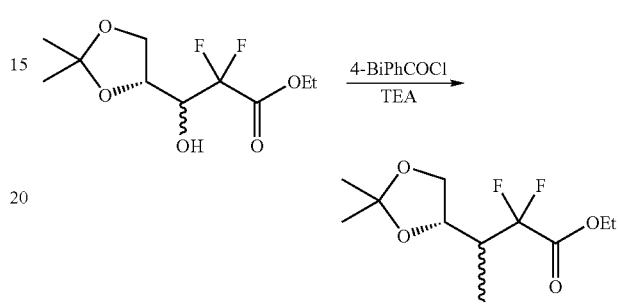

50.0 g of the compound obtained in Preparation 1 was added to 500 ml of methylene chloride, 42 ml of triethylamine and 51.1 g of 4-biphenylcarbonyl chloride were added thereto, and the mixture was kept at room temperature for 6 hours. After adding 360 ml of 1 N HCl thereto, the organic layer was successively washed with 180 ml portion of water, saturated sodium bicarbonate and NaCl, and dried over magnesiumsulfate. The residue was filtered, and distilled under a reduced pressure to obtain 83.7 g (yield 98%) of the title compound as a cream-color liquid.

NMR (300 MHz, CDCl$_3$): 1.25~1.74(m, 9H), 4.11~4.19 (m, 2H), 4.30~4.36(m, 2H), 4.56~4.58(m, 2H), 5.72~5.83 (ddd, 1H×⅓), 5.88~6.02(ddd, 1H×⅔), 7.42~7.53(m, 3H), 7.63~7.73(dd, 4H), 8.15~8.17(d, 2H)

EXAMPLE 2

Preparation of potassium 2,2-difluoro-3R-(4-biphenylcarbonyl)oxy-3-(2,2-dimethyl-[1,3]dioxoran-4-yl) propionate (the compound of formula (III); R=4-biphenylcarbonyl)

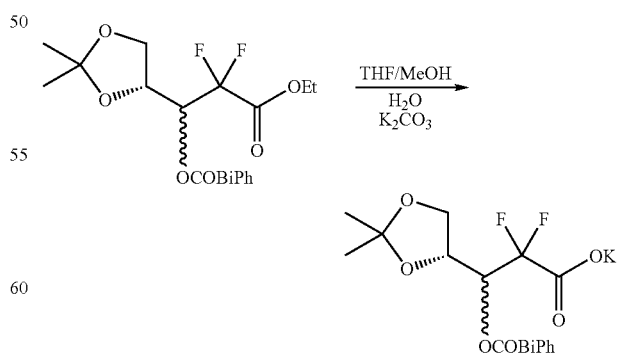

Method A 83.8 g of the compound obtained in Example 1 was added to 1.4 L of a mixture of tetrahydrofuran and methanol (2:3, v/v), and 107 g of potassium carbonate dissolved in 750 ml of water was added thereto. The mixture was stirred for 30 min, and kept under a reduced pressure to remove the organic solvent. After filtering, the solid was added to 100 ml of ether, stirred, filtered, washed with ether, and dried to obtain 60.1 g (yield 70%) of the title compound as a white solid.

HPLC: R-isomer 99.86%, S-isomer 0.11% NMR (300 MHz, DMSO): 1.07(s, 3H), 1.22(s, 3H), 3.99(t, 1H), 4.11(t, 1H), 4.49(t, 1H), 5.88(ddd, 1H), 7.38~7.54(m, 3H), 7.75(d, 2H), 7.85(d, 2H), 8.07(d, 2H)

Method B 94.0 g of the compound obtained in Example 1 was added to 600 ml of a mixture of tetrahydrofuran and methanol (1:1, v/v), and 54.4 g of potassium carbonate dissolved in 500 ml of water was added thereto. The mixture was stirred for 1 hour, washed twice with 500 ml portion of hexane, extracted with 500 ml of ethyl acetate, and kept under a reduced pressure to remove the solvent. The resulting solid was mixed with 100 ml of water and 300 ml of i-propyl alcohol, heated until it dissolved, and 700 ml of i-propyl alcohol was added thereto. The resulting mixture was kept at room temperature for 2 hours to allow the recrystallization of solids, which were filtered, washed with i-propyl alcohol, and dried to obtain 62.5 g (yield 65%) of the title compound as a white solid.

HPLC: R-isomer 99.91%, S-isomer 0.06% NMR (300 MHz, DMSO): 1.07(s, 3H), 1.22(s, 3H), 3.99(t, 1H), 4.11(t, 1H), 4.49(t, 1H), 5.88(ddd, 1H), 7.38~7.54(m, 3H), 7.75(d, 2H), 7.85(d, 2H), 8.07(d, 2H)

EXAMPLE 3

Preparation of D-erythro-2-deoxy-2,2-difluoro-pentofuranos-1-ulose-5-benzoyl-3-(4-phenyl)benzoate (the compound of formula (I); R=4-biphenyl-carbonyl, $R^3$=benzoyl)

Method A: Preparation by isolating each product of each step

Step 1: Preparation of D-erythro-2-deoxy-2,2-difluoro-pentofuranos-1-ulnose-3-(4-phenyl)benzoate (the compound of formula (II); R=4-biphenylcarbonyl)

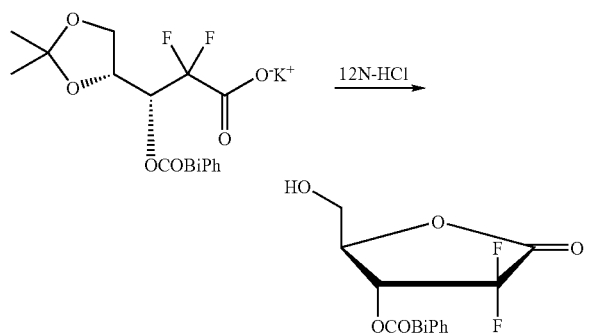

10 g of the compound obtained in Example 2 was dispersed in 60 ml of acetonitrile, 2.5 ml of 12 N HCl was added thereto, and the mixture was refluxed for 6 hours. 60 ml of toluene was added thereto, and the reaction mixture was distilled to remove the solvent. This procedure was repeated twice. 100 ml of ether was added to the residue, filtered to remove KCl, and distilled under a reduced pressure to remove the solvent. The resulting residue was added to 50 ml of ether, and 100 ml of hexane was added thereto to induce recrystallization of a solid. The solid was recovered by filtration (the first batch of solid); and the filtrate was distilled under a reduced pressure, and subjected to a second recrystallization step using 20 ml of ether and 50 ml of hexane to obtain a second batch of solid. The solids were combined, and dried under a vacuum to obtain 5.9 g (yield 75%) of the title compound as a white solid.

NMR (300 MHz, CDCl$_3$): 1.8~2.4(brd s, 1H), 3.78~4.02 (dd, 1H), 4.11~4.13(dd, 1H), 4.71~4.73(m, 1H), 5.79~5.87 (m, 1H), 7.44~7.54(m, 3H), 7.64~7.66(d, 2H), 7.21~7.75(d, 2H) Melting point (m.p.): 107~111° C.

Step 2: Preparation of D-erythro-2-deoxy-2,2-difluoro-pentofuranos-1-ulose-5-benzoyl-3-(4-phenyl)benzoate

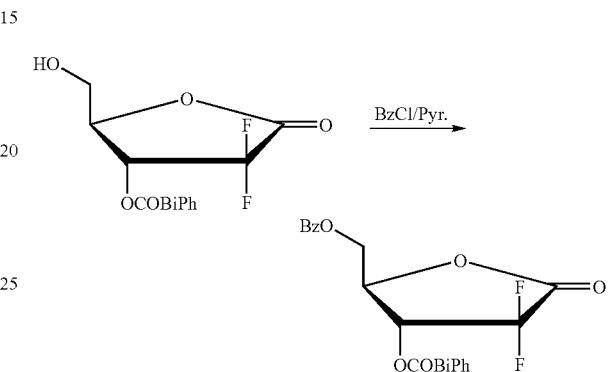

15.0 g of the compound obtained in Step 1 was added to 150 ml of methylene chloride, 6.9 ml of pyridine was added dropwise thereto with stirring at room temperature, and 7.4 ml of benzoyl chloride dissolved in 40 ml of methylene chloride was added thereto slowly while maintaining the temperature at 5 to 10° C. The reaction mixture was kept at room temperature for 7 hours, 105 ml of 1 N HCl was added thereto to neutralize pyridine in the mixture, and water added thereto to induce the separation of an organic layer. The organic layer was separated, washed successively with 100 ml portion of saturated sodium bicarbonate and NaCl, dried over magnesium sulfate, and filtered. The remaining solution was kept under a reduced pressure to obtain a cream-color solid. The solid was recrystallized from a mixture of ether and hexane (5:1, v/v) to obtain 16.8 g (yield 86%) of the title compound.

NMR (300 MHz, CDCl$_3$): 4.90~4.75(ddd, 2H), 5.10(dd, 1H), 5.87(ddd, 1H), 7.65~7.50(m, 5H), 7.78~7.67(m, 3H), 7.81(d, 2H), 8.13(d, 2H), 8.23(d, 2H) Melting point (m.p.): 130~131° C. HPLC purity: 99.21% (threo isomer was not found)

Method B: In situ Preparation

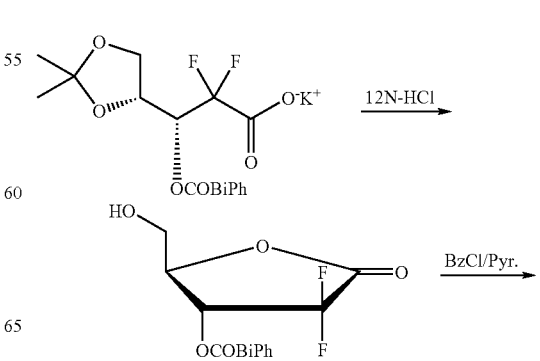

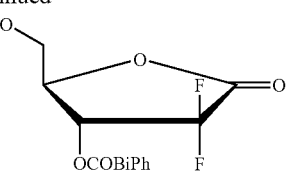

232 ml of acetonitrile was mixed with 38.8 g of the compound obtained in Example 2 and 9.2 ml of 12 N HCl, and the mixture was refluxed for 6 hours. After adding 464 ml of toluene thereto, the reaction mixture was distilled to remove water and acetonitrile until the temperature became over 100° C. The resulting concentrate was filtered and kept under a reduced pressure to obtain a foam-shaped solid. The solid was dissolved in 300 ml of ethyl acetate, 14 ml of pyridine was added thereto with stirring, and 15 ml of benzoyl chloride dissolved in 75 ml of ethyl acetate was added thereto. The mixture was kept at room temperature for 6 hours, and 210 ml of 1 N HCl was added thereto to neutralize pyridine. The organic layer was separated, washed successively with 150 ml portion of water, saturated sodium bicarbonate and NaCl, dried over magnesium sulfate, and kept under a reduced pressure to obtain a cream-color solid. The solid was recrystallized from a mixture of ether and hexane (5:1, v/v) to obtain 28.4 g (yield 72%) of the title compound as a white solid.

NMR (300 MHz, CDCl$_3$): 4.90~4.75(ddd, 2H), 5.10(dd, 1H), 5.87(ddd, 1H), 7.65~7.50(m, 5H), 7.78~7.67(m, 3H), 7.81(d, 2H), 8.13(d, 2H), 8.23(d, 2H) Melting point (m.p.): 130~131° C. HPLC purity: 99.05% (No threo isomer was detected)

EXAMPLE 4

Preparation of D-erythro-2-deoxy-2,2-difluoro-pentofuranos-1-ulose-3,5-di-(4-phenyl)benzoate (the compound of formula (I); R and $R^3$=4-bicarbonyl)

Method A: Preparation by isolating each product of each step

Step 1: Preparation of D-erythro-2-deoxy-2,2-difluoro-pentofuranos-1-ulose-3-(4-phenyl)benzoate (the compound of formula (II); R=4-biphenylcarbonyl)

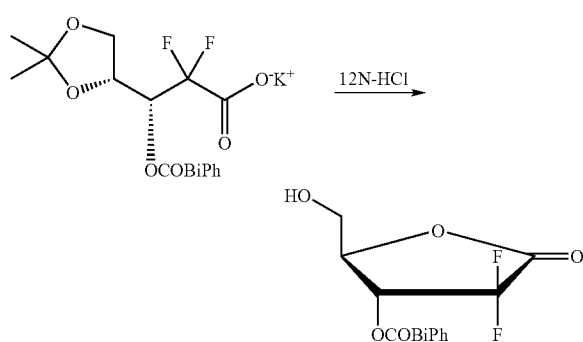

The procedure in Step 1 of Method A of Example 2 was repeated to obtain the title compound (yield 75%).

Step 2: Preparation of D-erythro-2-deoxy-2,2-difluoro-pentofuranos-1-ulose-3,5-di-(4-phenyl)benzoate

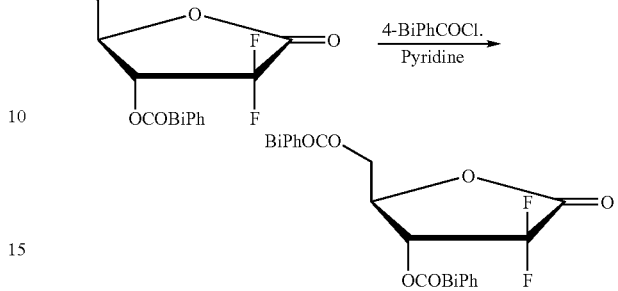

20 g of the compound obtained in Step 1 was added to 300 ml of chloroform, 9.5 ml of pyridine was added thereto with stirring at room temperature, and 10.1 ml of benzoyl chloride dissolved in 55 ml of chloroform was added thereto. The mixture was kept at room temperature for 6 hours, and the remaining pyridine was neutralized using 140 ml of 1N HCl. The organic layer was separated, successively washed with 150 ml portion of water, saturated sodium bicarbonate and NaCl, dried over magnesium sulfate, and kept under a reduced pressure to obtain a cream-color solid. The solid was recrystallized from a mixture of acetate and hexane (3:1, v/v) to obtain 21.8 g (yield 72%) of the title compound as a white solid.

NMR (300 M , CDCl$_3$): 4.72~4.79(m, 2H), 5.03(q, 1H), 5.84~5.76(m, 1H), 7.48~7.44(m, 6H), 7.72~7.60(m, 8H), 8.15~8.07(m, 4H) Melting point (m.p.): 137~139° C. HPLC purity: 98.95% (No threo isomer was detected)

Method B: In Situ Preparation

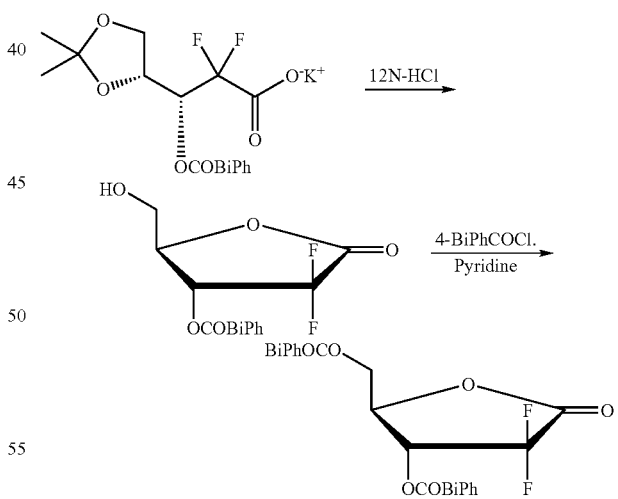

40.0 g of the compound obtained in Example 2 was added to 240 ml of acetonitrile, 10 ml of 12 N HCl was added thereto, and the mixture was refluxed for 6 hours. After adding 250 ml of toluene thereto, the reaction mixture was distilled to remove water and acetonitrile, cooled to room temperature, filtered, and kept under a reduced pressure to obtain 5-hydroxy-1-oxoribose as an intermediate. The intermediate was dissolved in 480 ml of ethyl acetate, a mixture of 21.8 ml of pyridine and 39 g of 4-biphenylcarbonyl chloride was added thereto, and allowed to react at room temperature for 12 hours. 320 ml of 1 N HCl was added to the reacting mixture to neutralize the remaining pyridine; the organic layer was separated, washed successively with 160 ml portion of water, saturated sodium bicarbonate and NaCl, dried, and filtered. The filtrate was kept under a reduced pressure to remove the solvent, and the residue was recrystallized from a mixture ethylacetate and hexane (3:1, v/v) to obtain 31.9 g (yield 65%) of the title compound as a white solid.

NMR (300 MHz, CDCl$_3$): 4.72~4.79(m, 2H), 5.03(q, 1H), 5.84~5.76(m, 1H), 7.48~7.44(m, 6H), 7.72~7.60(m, 8H), 8.15~8.07(m, 4H) Melting point (m.p.): 137~139° C. HPLC purity: 98.33 (No threo isomer was detected)

While the invention has been described with respect to the above specific embodiments, it should be recognized that various modifications and changes may be made to the invention by those skilled in the art which also fall within the scope of the invention as defined by the appended claims.

What is claimed is:

1. A method for preparing a 2,2-difluoro-2-deoxy-1-oxoribose derivative of formula (I), comprising the steps of:
   (i) reacting a compound of formula (V) with a biphenylcarbonyl derivative to obtain a compound of formula (IV) having the 3-hydroxy group protected by a biphenylcabonyl group;
   (ii) reacting the compound of formula (IV) with a base in a mixed solvent essentially comprising water and isolating a resulting 3R-carboxylate enantiomer of formula (III) by filtration;
   (iii) reacting the compound of formula (III) with an acid to obtain a 5-hydroxy-1-oxoribose derivative of formula (II); and
   (iv) protecting the 5-hydroxy group of the compound of formula (II) with R$^3$:

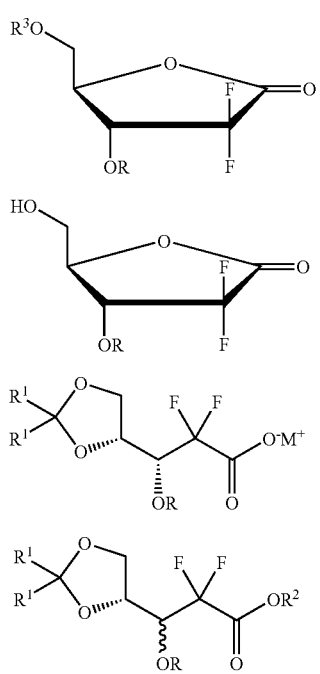

wherein,

R is

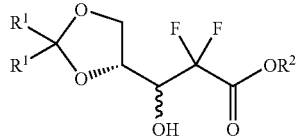

R$^1$ is methyl or ethyl;
R$^2$ C$_{1-3}$ alkyl;
r$^3$ is benzoyl or

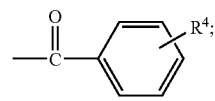

R$^4$ is phenyl or substituted phenyl; and
M is sodium or potassium.

2. The method of claim 1, wherein the biphenylcarbonyl group of step (i) is 2-biphenylcarbonyl or 4-biphenylcarbonyl.

3. The method of claim 1, wherein the mixed solvent essentially comprising water used in step (ii) is a mixture of water and an organic solvent selected from the group consisting of tetrahydrofuran, dioxane, acetonitrile, acetone, methylisobutylketone, methylethylketone, methanol, ethanol, propanol, isopropanol, dimethylacetamide, dimethylformamide, dimethylsulfoxide, ethylacetate and a mixture thereof 4. The method of claim 1, wherein the base used in step (ii) is selected from the group consisting of sodium carbonate, sodium bicarbonate, sodium hydroxide, potassium carbonate, potassium bicarbonate, potassium hydroxide and a mixture thereof.

5. The method of claim 4, wherein the base used in step (ii) is potassium carbonate.

6. The method of claim 1, wherein the acid used in step (iii) is selected from the group consisting of 1 to 12 N HCl, 1 to 9 N H$_2$SO$_4$, methanesulfonic acid, p-toluenesulfonic acid, trifluoroacetic acid and trifluoromethanesulfonic acid.

7. The method of claim 6, wherein the acid used in step (iii) is 12 N HCl.

8. The method of claim 1, wherein the acid used in step (iii) is employed in an amount ranging from 1.1 to 1.5 equivalents based on the compound of formula (II).

* * * * *